US006740762B2

(12) United States Patent
Zoeller et al.

(10) Patent No.: US 6,740,762 B2
(45) Date of Patent: *May 25, 2004

(54) PROCESS FOR ASCORBIC ACIDS USING ALKALINE EARTH SILICATE CATALYSTS

(75) Inventors: Joseph Robert Zoeller, Kingsport, TN (US); Allen Lynn Crain, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/213,736

(22) Filed: Aug. 7, 2002

(65) Prior Publication Data

US 2003/0073854 A1 Apr. 17, 2003

Related U.S. Application Data

(60) Provisional application No. 60/314,860, filed on Aug. 24, 2001, and provisional application No. 60/322,281, filed on Sep. 14, 2001.

(51) Int. Cl.$^7$ .............................................. C07D 307/62
(52) U.S. Cl. ........................................................ 549/315
(58) Field of Search ............................................ 549/315

(56) References Cited

U.S. PATENT DOCUMENTS

| 2,265,121 A | 12/1941 | Reichstein |
| 2,462,251 A | 2/1949 | Bassford, Jr. et al. |
| 2,491,065 A | 12/1949 | van Eekelen et al. |
| 4,767,870 A | 8/1988 | Fujiwara et al. |
| 5,128,487 A | 7/1992 | Tomislav et al. |
| 5,391,770 A | 2/1995 | Le Fur et al. |
| 5,744,618 A | 4/1998 | Fechtel et al. |
| 5,817,238 A | 10/1998 | Makino et al. |

FOREIGN PATENT DOCUMENTS

| DE | 38 43 389 A1 | 6/1990 |
| EP | 0 554 090 A2 | 8/1993 |
| GB | 428814 | 5/1935 |
| GB | 428815 | 5/1935 |
| GB | 1 222 322 A | 2/1971 |
| GB | 2 034 315 A | 6/1980 |
| JP | 73015931 B | 5/1973 |
| WO | WO 87/00839 A1 | 2/1987 |
| WO | WO 97/13761 A1 | 4/1997 |
| WO | WO 99/07691 A2 | 2/1999 |
| WO | WO 00/46216 A1 | 8/2000 |

OTHER PUBLICATIONS

T. Reichstein et al., *Helv. Chim. Acta* 17, (1934), pp. 311–328.
Crawford et al. *Adv. Carbohydrate Chemistry*, 37 (1980), pp. 79–155.

*Primary Examiner*—Taofiq Solola
(74) *Attorney, Agent, or Firm*—Eric D. Middlemas; Bernard J. Graves, Jr.

(57) ABSTRACT

Disclosed is a process for the preparation of ascorbic acids from 2-keto-hexonic acids or 2-keto-hexonic acid derivatives using alkaline earth silicate catalysts. The process may be carried out in water, alcohols, or in a variety of polar or moderately polar solvents or solvent mixtures and provides for simple workup and purification of ascorbic acid products. The process generates no by-product salts and thus, does not require the steps of neutralization or the handling of salt by-products. The process is particularly suited for the continuous preparation of L-ascorbic acid from 2-keto-L-gulonic acid and its esters.

15 Claims, No Drawings

US 6,740,762 B2

PROCESS FOR ASCORBIC ACIDS USING ALKALINE EARTH SILICATE CATALYSTS

This application claims the benefit under 35 U.S.C. §119(e) of U.S. Provisional Application Serial No. 60/314,860, filed Aug. 24, 2001, and of U.S. Provisional Application Serial No. 60/322,281, filed Sep. 14, 2001. The disclosure of provisional applcations 60/314,860 and 60/322,281 is hereby incorporated herein by reference.

FIELD OF THE INVENTION

The present invention pertains to a process for producing ascorbic acids. Specifically, the present invention pertains to a process for preparing ascorbic acids from 2-keto-hexonic acids in the presence of alkaline earth silicates as catalysts.

BACKGROUND OF THE INVENTION

L-Ascorbic acid (vitamin C) is produced commercially by a combination of chemical and fermentation processes starting from glucose or sorbose. These processes first produce a 2-keto-hexonic acid which subsequently may be cyclized through a lactonization reaction to an ascorbic acid. For example, a common 2-keto-hexonic acid generated in the commercial ascorbic process is 2-keto-L-gulonic acid (2-KLG) or its protected form, diacetone-2-keto-L-gulonic acid. The 2-keto-L-gulonic acid then may be converted to L-ascorbic acid by esterification with methanol, followed by cyclization using stoichiometric amounts of a base, in a procedure originally reported by Reichstein (T. Reichstein and A. Grussner, *Helv. Chim. Acta* 17, (1934), p. 311–328). A stoichiometric amount of base is normally required for cyclization of the ester because an equivalent of base is consumed to generate the corresponding salt of L-ascorbic acid. The formation of this salt requires a subsequent acidification step to liberate the desired L-ascorbic acid product.

Improvements to the Reichstein process have often involved removal or simplification of many of the chemical processing steps required for the production of 2-keto-L-gulonic acid. Examples of such improvements include controlled esterification of 2-keto-L-gulonic acid and subsequent removal of unesterified starting material, as described in U.S. Pat. No. 5,128,487, and integration of esterification and lactonization steps, described in U.S. Pat. No. 5,391,770.

Esterfication may be avoided by conducting the lactonization in the presence of acid catalysts as described in U.S. Pat. No. 2,462,251; UK Patent Application No. 2,034,315 A; International Patent Application No. 99/07691; International Patent Application No. 00/46216, and Crawford et al. *Adv. Carbohydrate Chemistry*, 37 (1980), pp. 79–155. With acid catalysts, 2-keto-hexonic acids, their corresponding acetals, or ketals may be cyclized directly, with consecutive lactonization and enolization, to form ascorbic acids. For example, 2-keto-L-gulonic acid may be cyclized in the presence of acid catalysts to produce L-ascorbic acid. This process eliminates the need for the generation of the ester and subsequent steps requiring the addition of stoichiometric base for cyclization with reprotonation of the ascorbate salt. Alternatively, diacetone-2-keto-L-gulonic acid may be cyclized, with loss of acetone, to form L-ascorbic acid. Direct cyclization of diacetone-2-keto-L-gulonic acid, however, requires extensive purification for recovery of the acetone and other by-products generated. Additional modifications have been described to improve acid catalyzed processes such as the use of organic solvents and surfactants as described in U.S. Pat. No. 5,744,618; International Patent Application No. 87/00839; and Japan Patent No. 73015931. Although these modification have provided improvements to the original Reichstein process, significant handling, recycling, and purification steps are needed to obtain a high yield of ascorbic acid.

The lactonization of 2-keto-hexonic acids also has been accomplished using solid acid catalysts. UK Patent No. 1,222,322 discloses the use of an acidic resin catalyst for conversion of 2-keto-hexonic acids to ascorbic acids. A similar use of acidic zeolites is described in German Patent Application No. 3843389 A1. These processes, however, cannot be operated in water and require the use of non-reactive organic solvents to prevent hydrolysis of 2-keto-hexonic acid ester starting materials. Additional processing steps, therefore, are required to remove, dispose of, and recycle the organic solvents. In addition, the yields from acid catalyzed processes are often low because of decomposition of the ascorbic acid.

It is also known that ascorbic acid may be prepared from 2-keto-L-gulonic acid without the use of strong acid catalysts (see T. Reichstein, *Helv. Chim. Acta* 17, 1934, pp. 311–328 and UK Patent No. 428,815) by thermal cyclization in water (U.S. Pat. No. 2,491,065) or by heating 2-keto-L-gulonic acid in water saturated with carbon dioxide (U.S. Pat. No. 2,265,121). Although avideing extensive purification steps, these processes provide uneconomically low yields of ascorbic acid.

It is evident that the existing process for converting 2-keto-hexonic acids, including 2-keto-L-gulonic acid, and their derivatives to ascorbic acids suffer either from low yields or require the use of organic solvents and extensive processing to obtain ascorbic acid products of acceptable purity. Thus a need exists for an efficient and economical process for the preparation of ascorbic acids from 2-keto-hexonic acids that avoids many of the problems inherent in the aforementioned processes. In addition, it would be useful to develop a method of catalytic ring closure for the conversion of 2-keto-hexonic acids and their derivatives to ascorbic acids that avoids the generation of by-product salts and eliminates the need for neutralization and handling of salt by-products. Even more advantageous would be the development of a process employing a heterogeneous catalyst that would enable simple and rapid separation of the catalyst from the product mixture and, thus, provide a means to conduct the preparation of ascorbic acids in a continuous manner.

SUMMARY OF THE INVENTION

The present invention provides a process for the preparation of ascorbic acids from 2-keto-hexonic acids or 2-keto-hexonic acid derivatives using basic, heterogeneous catalysts. Thus, one embodiment of the present invention is a process for preparing an ascorbic acid comprising contacting a 2-keto-hexonic acid, a 2-keto-hexonic acid derivative, or a mixture thereof with a catalyst comprising at least one alkaline earth silicate. Our process is suitable for a wide range of ascorbic acid precursors including 2-keto-hexonic acids, acetals, ethers, ketals, and esters. The alkaline earth silicate catalysts of the present invention are widely available, may be obtained at low cost, are operable over a wide temperature range, and can readily regenerated if necessary by high temperature or oxidative regeneration. Because the present invention employs a heterogeneous catalyst, separation of the product mixture from the catalyst is simple and rapid. Our invention may be carried out in water or in a variety of polar or moderately polar solvents or solvent mixtures and provides for simple workup and purification of ascorbic acid products. Our process generates no by-product salts and, thus, does not require the steps of neutralization or the handling of copious amounts of salt by-products.

Another embodiment of the present invention pertains to a process for the continuous preparation of L-ascorbic acid comprising the steps of (i) continuously feeding a water, methanol, or ethanol solution comprising a 2-KLG reactant selected from the group consisting of 2-KLG, the methyl ester of 2-KLG, the ethyl ester of 2-KLG, and mixtures thereof to a reactor operated under substantially plug-flow conditions and maintained at reaction conditions of temperature and pressure; (ii) contacting the feed solution from step(i) with a catalyst selected from the group consisting of a calcium silicate, a calcium-magnesium silicate, a magnesium silicate, and mixtures thereof wherein a portion the 2-KLG reactant is reacted to form L-ascorbic acid; (iii) continuously removing a solution comprising L-ascorbic acid and unreacted 2-KLG reactant from the reactor; (iv) separing and recovering the unreacted 2-KLG reactant from the L-ascorbic acid to produce an enriched L-ascorbic acid and a solution comprising the 2-KLG reactant; and (v) recycling the recovered 2-KLG reactant solution of step(iv) to step(i). The present invention provides for continuous production of L-ascorbic acid which affords increased efficiency of conversion with no loss of selectivity of product formation and recycling of the unreacted 2-KLG reactants. The method also is suited for use under plug flow reaction conditions which allow for controlled synthesis and simple isolation of L-ascorbic acid.

DETAILED DESCRIPTION

The present invention is a process for preparing an ascorbic acid comprising contacting a 2-keto-hexonic acid, a 2-keto-hexonic acid derivative, or a mixture thereof with a catalyst comprising at least one alkaline earth silicate. The alkaline earth metals used in the present invention include berylium, magnesium, calcium, strontium, and barium. The conversion may be performed using aqueous or polar organic solvents and eliminates the need for neutralization and separation of salt intermediates. In one embodiment, L-ascorbic acid may be synthesized from 2-keto-L-gulonic acid directly, or from 2-keto-L-gulonic acid derivatives such as 2-keto-L-gulonic acid esters, diacetone-2-keto gulonic acid, methylene ethers of 2-keto-L-gulonic acid, and the like. Unlike earlier processes for this lactonization under basic conditions, the process of the present invention is catalytic. In addition, the method is suited for use in reactors operating under plug flow conditions, and is particularly useful for the preparation and isolation of L-ascorbic acid from 2-keto-L-gulonic acid or an ester of 2-keto-L-gulonic acid with recycling of the unreacted 2-keto-L-gulonic acid or ester thereof. When 2-keto-L-gulonic acid is used directly, the need to generate the ester intermediate is avoided.

The process of the present invention may be used to prepare an ascorbic acid. The term "ascorbic acid" as used in the present invention, means any compound containing an ascorbate radical represented by the formula:

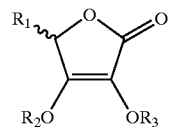

wherein $R_1$ represents a 2 carbon group which, in turn, may be substituted with hydrogen, hydroxy, alkoxy, aryloxy, carboxyl, cycloalkoxy, sulfinato, sulfonato, phosphate, keto, or aldehydo groups; $R_2$ and $R_3$ represent hydrogen, an alkali metal or alkaline earth metal cation from Group 1 or 2 of the Periodic Table of the Elements, the same or different hydrocarbyl groups, or $R_2$ and $R_3$ may separately or in combination represent joined groups constituting a hydrocarbylene group containing from 1 up to about 6 carbon atoms. Preferably, $R_2$ and $R_3$ may contain a total carbon content of up to about 12 carbon atoms. Specific examples of alkali and alkaline earth metal cations are sodium, lithium, potassium, cesium, rubidium, berylium, magnesium, calcium, strontium, and barium. Non-limiting examples of hydrocarbyl and hydrocarbylene groups which $R_2$ and $R_3$ separately or together may represent include methyl, ethyl, butyl, pentyl, hexyl, 2-ethylhexyl, octyl, methylene, dimethylmethylene, ethylethylene, trimethylene, tetramethylene, and various isomers thereof. The hydrocarbyl and hydrocarbylene groups may in turn carry additional substituents such as alkoxy, cycloalkoxy, alkanoyl, aryl, formyl, aroyl, carboxyl, carboxylate salts, alkoxycarbonyl, alkanoyloxy, cyano, sulfonic acid, sulfonate salts, and the like. Examples of ascorbic acids include, but are not limited to, levo-ascorbic acid ("L-ascorbic acid" or "Vitamin C"), dextro-ascorbic acid ("D-ascorbic acid"), D-araboascorbic acid (also known as erythorbic acid, D-erythroascorbic acid, or isoascorbic acid), 5-keto-L-ascorbic acid, and 6-aldehydo-L-ascorbic acid. For the process of the prensent invention, L-ascorbic acid and D-araboascorbic acid are most preferred.

Our invention employs a 2-keto-hexonic acid, a 2-keto-hexonic acid derivative, or a mixture thereof as a reactant. As used in the present invention, the term 2-keto-hexonic acid means any polyhydroxy, linear hexoic acid carrying a keto substituent α to or adjacent to the carboxylic acid carbon and a hydroxyl group on carbon 4 (where the carboxylic acid carbon is carbon 1) or γ to the carboxylic acid group. Examples of 2-keto-hexonic acids include but are not limited to 2-keto-L-gulonic acid, 2-keto-D-gluconic acid, 2,5-diketogluconic acid, and 2-keto-L-galactonic acid. The preferred 2-keto-hexonic acids are 2-keto-L-gulonic acid (referred to herein as "2-KLG") and 2-keto-D-gluconic acid (referred to herein as "2-KDG"); however, 2-keto-gulonic acid is the especially preferred reactant.

Alternatively, a 2-keto-hexonic acid derivative or a mixture of a 2-keto-hexonic acid and a 2-keto-hexonic acid derivative may used as reactants in the present invention. Suitable 2-keto-hexonic acid derivatives include esters, acetals, hemiacetals, ketals, hemiketals, or ethers. Preferred 2-keto-hexonic acid derivatives are 2-keto-L-gulonic acid derivatives such as 2-keto-L-gulonic acid esters, diacetone-2-keto gulonic acid, methylene ethers of 2-keto-L-gulonic acid, and the like. Preferably, the derivative is an alkyl ester of a 2-keto-hexonic acid wherein the alcohol component of the ester is represented as an alkoxy radical. Thus, as used herein, the term "alkoxy" refers to the "RO—" radical where R is a straight or branched chain hydrocarbon having from 1 up to about 12 carbon atoms, which may carry 1 or more substituents such as alkoxy, cycloalkyl, cycloalkoxy, alkanoyl, aryl, aryloxy, aroyl, carboxyl, and the like. Non-limiting examples of alkyl groups are methyl, ethyl, propyl, isopropyl, n-butyl, isobutyl, 2-ethylhexyl, octyl, nonyl, hexyl, and the various isomers thereof. It is preferred that the alkyl group of the ester contains from 1 up to about 4 carbon atoms. Most preferably, the alkyl group of the ester contains from 1 up to about 2 carbon atoms. The preferred 2-keto-hexonic acid esters are the methyl and ethyl esters of 2-KLG and 2-KDG. The methyl and ethyl ester of 2-KLG are peferred.

The source of the 2-keto-hexonic acid or 2-keto-hexonic acid derivative is unimportant in the process. Many 2-keto-hexonic acids and derivative are available commercially. For example, the methyl ester of 2-keto-L-gulonic acid (methyl 2-keto-L-gulonate) may be purchased commercially (Aldrich Chemical Co., Milwaukee, Wis.). The 2-keto-hexonic acids and their derivatives may be prepared by synthetic organic chemistry procedures well known to persons skilled in the art and published in chemical journals. Synthethic procedures for various 2-keto-hexonic acids, for example, are reviewed in Crawford et al. *Adv. Carbohydrate Chemistry*, 37 (1980), pp. 79–155. Alternatively, the 2-keto-hexonic acids or derivatives thereof may be prepared by a fermentation process, by cultivation of one or more microorganisms in aqueous media. In a fermentation process, 2-keto-hexonic acid or keto-hexonic acid derivative are produced in an aqueous fermentation broth that typically contains other dissolved materials such as nutrients required by the active microorganism(s) including, for example, amino acids, inorganic and organic salts, carbohydrates such as glucose, sorbose, mannose, disaccharides, and trisaccharides, depending upon the sugar feedstock to the fermenter and the various growth factors. The fermentation broth, containing the 2-keto-hexonic acid and/or keto-hexonic acid derivative is typically filtered to remove biomass and other insoluble materials and decolorized with activated charcoal. The fermentation broth may be used directly as feed to the process of the present invention or, preferably, concentrated to achieve a desired concentration of 2-keto-hexonic acid by evaporating or distilling away a portion of the water present before use as a feedstock. Alternatively, the 2-keto-hexonic acid or derivative thereof may by converted to another compound or derivative before use in the present invention. For example, in one embodiment, 2-keto-L-gulonic acid may be obtained by fermentation of sorbose or glucose followed by a preliminary purification process to remove solids. An initial purification of this filtrate, for example, by electrodialysis, ion exchange, or crystallization, may be undertaken, but is not a precondition for the operation this invention. The 2-keto-L-gulonic acid may then be used directly, or may be converted into an ester form.

The process of the present invention may carried in a variety of solvents. The selection of a solvent or a solvent mixture is limited only by the solubility of the 2-keto-hexonic acid and ascorbic acid products. Preferably, the solvent is polar or moderately polar, or may be a mixture of various solvents that are capable of dissolving the reactants and products. As defined herein, the term "polar" means the solvent is comprised of molecules which exhibit properties consistent with a permanent, moderate to high dipole moment and possess a moderate to high dielectric constant. By contrast a "non-polar" solvent comprises molecules which do not exhibit or have a low dipole moment, and have a low dielectric constant. In the present invention, a solvent exhibiting a dielectric constant greater than 2 is considered to be polar. Non-limiting examples of polar or moderately polar solvents which may be used in our process include water, alcohols, diols, esters, ethers, amides, sulfoxides, sulfones, nitrites, ketones, aldehydes, and mixtures thereof. Preferably, the solvent is an alcohol. Examples of alcohols which may be used as solvents include but are not limited to methanol, ethanol, propanol, n-butanol, isobutanol, isopropanol, 2-butanol, n-hexanol, octanol, and the various isomers thereof. In the case where an alkyl ester of a 2-keto-hexonic acid is used, it is preferred that the alcohol solvent correspond to the alkoxy component of the 2-keto-hexonic acid ester. Even more preferably, the solvent is ethanol or methanol. The most preferred solvent is water.

The process of the present invention employs an alkaline earth silicate catalyst. The catalyst may be a composition containing one or more alkaline earth components and silica or may be a mixture of compositions containing one or more alkaline earth silicates. By the term "alkaline earth silicate", it is meant any compound or composition containing silicon, oxygen, and one or more alkaline earth metals or alkaline earth metal compounds. Typically, the alkaline earth silicate catalyst comprises an alkaline earth metal or alkaline earth metal compound admixed with, impregnated into, ion-exchanged with, coprecipitated with, deposited on, or supported on a silica. The terms "alkaline earth", "alkaline earth metal", or "alkaline earth component", used herein, mean an element or a compound of an element selected from Group 2 (IIA) of the Periodic Table of the Elements. Alkaline earth metals include beryllium, magnesium, calcium, strontium, barium and radium. The term "silica" is defined and used herein as any form of silicon dioxide in anhydrous, hydrated, or partially hydrated form, or as any compound having the general formula $SiO_2$. Examples of silica include materials referred to a silica, silicic acid, silica gel, silicon dioxide, amorphous silica, silicate, fumed silica, and the like. The preferred the alkaline earth components of the catalyst include barium, strontium, magnesium, or calcium, compounds thereof, either alone or as a mixture of components thereof. More preferably, the alkaline earth component is magnesium, or calcium, or a mixture thereof.

The alkaline earth silicates used in the present invention are known materials and may be prepared by procedures well known by practitioners skilled in the art (see, for example, van Santen et al. *Catalysis: An Integrated Approach*, $2^{nd}$ Ed., (Amsterdam: Elsevier, 1999), Chapters 9 & 10). By the term "silicate," it is meant orthosilicates, the metasilicates, and the trisilicates, and include the hydrated, partially hydrated, and anhydrous forms of any of these silicates. Nonlimiting examples of the alkaline earth silicates are beryllium disilicate ($Be_4Si_2O_7(OH)_2$), beryllium orthosilicate ($Be_2SiO_4$) ; magnesium metasilicate ($MgSiO_3$), magnesium orthosilicate ($Mg_2SiO_4$); calcium α-metasilicate and calcium β-metasilicate ($CaSiO_3$), calcium diorthosilicate ($Ca_2SiO_4$), calcium trisilicate ($Ca_3SiO_5$) which is sometimes written ($3CaOSiO_2$); strontium metasilicate ($SrSiO_3$); strontium orthosilicate ($SrSiO_4$); barium metasilicate ($BaSiO_3$); as well as the hydrates such as ($BaSiO_3.6H_2O$), and the like. Alkaline earth silicates are readily available commercially with a wide range of compositions and may be obtained from natural mineral sources. Examples of naturally occurring alkaline earth silicates include entastite ($MgSiO_3$), talc ($Mg_3Si_4O_{10}$), serpentine ($Mg_2Si_2O_5(OH)_2$), wollastonite ($CaSiO_3$), diopside ($CaMgSi_2O_6$), akermanite ($Ca_2MgSi_2O_7$), clinoenstatite ($MgSiO_3$), forsterite ($Mg_2SiO_4$), phenakite ($Be_2SiO_4$), bertrandite ($Be_4Si_2O_7(OH)_2$), montcellite ($CaMgSiO_4$), and the like. Naturally occurring mixtures, manufactured mixtures, or chemically combined alkaline earth silicates such as diopside CaMg ($SiO_3$)$_2$ or mellilite $Ca_2MgSi_2O_7$ also are effective catalysts. Synthetic or manufactured magnesium silicates are sold under several trademarks, examples being FLORISIL® magnesium silicate (15 wt. % MgO: 85 wt. % $SiO_2$, U.S. Silica, Berkeley Springs, W. Va.) and MAGNESOL® magnesium silicate (1 MgO: 2.6 $SiO_2$ .H2O, The Dallas Group of America, Jeffersonville, Ind.). Manufactured calcium silicates are generally sold as powders with several trademarks, one example being MICRO-CEL® silicates (World Minerals, Santa Barbara, Calif.). Generally, the manufactured magnesium and calcium silicates are preferred since they allow close control of purity, stoichiometry, and other physical properties, such as pore size and surface area.

The alkaline earth silicon silicates of the present invention are not necessarily pure materials and may contain other elements and compounds without adverse effects. Several naturally occurring alkaline earth silicates having elements other than alkaline earth metals include the mixed iron/magnesium silicates, olivine and orthopyroxene, rhodonite (a mixed manganese, iron, calcium silicate), and tremolite (a partially fluorinated mixed calcium/magnesium silicate). Further, manufactured alkaline earth silicates often contain residual impurities introduced in the manufacturing process. For example, the commercially available FLORISIL® magnesium silicate may contain up to 0.5 wt. % $Na_2SO_4$. The presence of these impurities or the presence of carbonate on or within the alkaline earth silicate catalyst is not necessarily deleterious to performance, although in the case of iron or manganese containing minerals, extra care may be necessary to avoid the presence of oxygen which might lead to oxidation of the ascorbic acid product.

The gram-atom ratio of alkaline earth metal to silicon within the alkaline earth silicate catalyst may vary over a wide range of 1:20 to 20:1 gram-atom alkaline earth metal: gram-atom silicon. The gram-atom ratio of alkaline earth metal:silicon is more preferably, from 1:10 to 10:1, and even more preferably from 1:5 to 5:1. For example, the calcium and magnesium silicates listed above range in composition from a 1:3.8 (Mg:Si) for FLORISIL® magnesium silicate to a ratio of 2:1 (Ca+Mg: Si) for the naturally occurring calcium-magnesium silicate montcellite.

Generally, the alkaline earth silicates of the present invention are porous materials with large surface areas typically in a range of from about 0.5 $m^2$/g up to about 1000 $m^2$/g. The determination of the surface area of the alkaline earth silicates may be accomplished by standard gas adsorption techniques, for example, by the BET method (see van Santen et al. *Catalysis: An Integrated Approach*, $2^{nd}$ Ed., (Amsterdam: Elsevier, 1999), Chapter 13), that are well known to persons skilled in the art. Preferably, the alkaline earth silicates used in the present invention have surface areas in the range from about 50 $m^2$/g up to about 1000 $m^2$/g with a range of about 50 $m^2$/g up to about 300 $m^2$/g are particularly preferred. Typical surface areas for preferred commercial manufactured magnesium and calcium silicates are in the range of 75 $m^2$/g to 300 $m^2$/g. For example, the commercially available FLORISIL® magnesium silicate exhibits a surface area of about 150 up to about 280 $m^2$/g with a surface area of 220 $m^2$/g being typical.

Alkaline earth silicates can be obtained or generated in a variety of particle sizes. For example, the commercially manufactured FLORISIL® magnesium silicate is available in a variety of particle sizes ranging from a coarse grade of about 1.18 mm up to about 2.36 mm (8–16 mesh) to an extremely fine grade (<45 μm, >325 mesh). However, alkaline earth silicates are most commonly available as fine powders, with materials <45 μm (>325 mesh) available in a wide variety of compositions.

For the purpose of the present invention, any particle size for the alkaline earth silicate catalyst may be used. The particle size is selected on the basis of the type of reactor and reaction conditions used and may range from about 10 μm up to about 25 mm. Examples of reactor configurations suitable in the process of this invention are continuous stirred tank reactors, slurry reactors, fluidized beds, simulated moving bed reactors, and trickle bed reactors. For example, in fluidized beds or continuous stirred tank reactors, finer particles are preferred since finer particles facilitate dispersion throughout the reactor. In this embodiment, the particle size may range from about 10 μm up to about 25 mm, depending upon the application. It is preferred to operate our process using a plug flow reactor and, in this embodiment, larger particles are generally preferred to minimize pressure drop and reactor plugging. Therefore, the preferred particle size for a plug flow reactor would be the range of about 150 μm up to about 12 mm, with the range of about 500 μm up to about 5 mm especially preferred.

The alkaline earth silicate catalysts also may be used as chips or shaped particles of various dimensions, including rings, pellets, stars, and the like through standard catalyst forming techniques well known to persons skilled in the art. Examples of catalyst forming techniques include adding binders, extrusion, heat, pressure or a combination thereof.

The reaction conditions of temperature and pressure are not critical for the operation of the present invention. The reaction temperature and pressure used will depend on 2-keto-hexonic acid or 2-keto-hexonic acid derivative and the reactor configuration used in the process. Although the reaction may be conducted over a temperature range from about 25° C. up to about 250° C., the preferred range is from about 75° C. up to about 200° C. with the most favored reaction temperatures in the range of about 100° C. up to about 175° C.

The reaction also may be operated wide range of pressures from about 0.1 bars absolute up to about 100 bars absolute ("bara"). The choice of reaction pressure is dependent on the desired operating temperature, the solvent, or possibly, the reactor configuration. For example, in a trickle bed reactor, the pressure should be sufficient to prevent boiling within the catalyst bed. The preferred operating pressure is in the range of about 0.7 bara up to about 60 bara (approximately 10–870 psia) and more preferably, 1 bara up to about 40 bara (approximately 14.5–580 psia). For example, using the preferred methyl ester of 2-keto-L-gulonic acid and methanol as solvent, at 200° C., the pressure would be about 39 bara (approximately 570 psia), but when operated at 100° C., the pressure would be about 3.9 bara (approximately 56 psia). For aqueous solutions of 2-keto-L-gulonic acid within a temperature range of 75–200° C., the operating pressure will be in the range of about 0.7 bara up to about 17 bara (approximately 10–250 psia).

A preferred embodiment of the present invention is a process for the preparation of L-ascorbic acid comprising contacting a water, methanol, or ethanol solution comprising a 2-KLG reactant with a catalyst comprising at least one alkaline earth silicate wherein the gram-atom ratio of alkaline earth metal to silicon is in the range of about 1:5 to about 5:1 gram-atom alkaline earth metal:gram-atom silicon. The preferred surface area of the catalyst is in the range of about 50 $m^2$/g up to about 300 $m^2$/g. In this embodiment, the 2-KLG reactant may be 2-KLG, the methyl ester of 2-KLG, the ethyl ester of 2-KLG, or mixtures thereof. The preferred alkaline silicate catalyst is a composition or a mixture of compositions comprising at least one compound of magnesium and silica, calcium and silica, or mixtures thereof, Although not critical to the operation of this invention, the process of the present invention is preferably conducted under a substantially inert atmosphere in which the concentration of oxygen is less than about 0.1% by volume. Anaerobic storage/reaction conditions are generally accomplished by using inert gas such as carbon dioxide, helium, nitrogen, argon, among other gases, often under slightly elevated pressures.

The present invention includes continuous, semi-continuous, and batch modes of operation and may utilize a variety of reactor types. Examples of suitable reactor types include, but are not limited to, stirred tank, continuous stirred tank, trickle bed, tower, slurry, tubular, fluidized bed, and simulated moving bed reactors. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

A particularly preferred embodiment of the present invention is a process for the continuous preparation of L-ascorbic acid comprising the steps of (i) continuously feeding a water, methanol, or ethanol solution comprising a 2-KLG reactant selected from the group consisting of 2-KLG, the methyl ester of 2-KLG, the ethyl ester of 2-KLG, and mixtures thereof to a reactor operated under substantially plug-flow conditions and maintained at reaction conditions of temperature and pressure; (ii) contacting the feed solution from step(i) with a catalyst selected from the group consisting of a calcium silicate, a calcium-magnesium silicate, a magnesium silicate, and mixtures thereof wherein a portion the 2-KLG ester is reacted to form L-ascorbic acid; (iii) continuously removing a solution comprising L-ascorbic acid and unreacted 2-KLG reactant from the reactor; (iv) separating and recovering the unreacted 2-KLG reactant from the L-ascorbic acid to produce an enriched L-ascorbic acid and a solution comprising the 2-KLG reactant; and (v) recycling the recovered 2-KLG reactant solution of step(iv) to step(i).

A preferred feed comprises a water, methanol, or ethanol solution comprising a 2-KLG reactant which may be 2-KLG, the methyl ester of 2-KLG, or the ethyl ester of 2-KLG, or a mixture thereof, to a reactor operated under substantially plug flow conditions. The 2-KLG reactant may be obtained from any source but a preferred source of the 2-KLG reactant is from a fermentation process as described hereinabove. Although any concentration of the 2-KLG reactant may be used as long as the reactant remains in solution, concentrations of the 2-KLG reactant of about 1 up to about 40 weight percent are preferred. If the reactant is an aqueous solution of 2-KLG, then concentrations of about 5 up to about 30 weight percent 2-KLG are preferred, with 2-KLG concentration of about 8 up to 25 weigth percent being especially preferred.

A reactor operating under substantially plug flow conditions is particularly suited for our invention as it presents reaction conditions which allow for removal of the L-ascorbic acid within a kinetic time frame that prevents excessive degradation of the L-ascorbic acid product. Under plug flow conditions, the 2-KLG reactant feed solution is continuously passed through a reactor packed with a catalyst as a singular mix, or "plug" with little or no backmixing such that the concentrations of L-ascorbic acid in the effluent of the reactor are increased relative to the concentrations of L-ascorbic acid in the influent to the reactor. A variety of reactor types, including trickle bed, tower, slurry, tubular, fluidized bed, and simulated moving bed reactors may be used under plug flow conditions in the present invention. Particularly preferred reactor types are trickle bed, tubular, and simulated moving bed reactors.

The solution of 2-KLG reactant is contacted within the reactor with a catalyst comprising a calcium silicate, a calcium-magnesium silicate, a magnesium silicate, and mixtures thereof Preferred catalysts include both commercially manufactured and naturally occuring silicates. Examples of catalysts which are particularly preferred include, but are not limited to, entastite ($MgSiO_3$), talc ($Mg_3Si_4O_{10}$), terpentine ($Mg_2Si_2O_5(OH)_2$), tollaston ($CaSiO_3$), diopside ($CaMgSi_2O_6$), akermanite ($Ca_2\ MgSi_2O_7$), montcellite ($CaMgSiO_4$), FLORISIL® magnesium silicate (15 wt. % MgO: 85 wt. % $SiO_2$, US Silica, Berkeley Springs, W. Va.), MAGNESOL® magnesium silicate (1 MgO: 2.6 $SiO_2.H_2O$, The Dallas Group of America, Jeffersonville, Ind.), and MICRO-CEL® calcium silicate (World Minerals, Santa Barbara, Calif.). Especially preferred catalysts are magnesium silicates comprising about 15 wt. % MgO: 85 wt. % $SiO_2$, magnesium silicates comprising the general formula 1 MgO: 2.6 $SiO_2.H_2O$, and calcium silicates.

The reactor may be operated over a temperature range from about 25° C. up to about 250° C.; however, the preferred range is from about 75° C. up to about 200° C. with the most preferred reaction temperature in the range of about 100° C. up to about 175° C. The choice of reaction pressure is dependent on the desired operating temperature, the solvent, and the reactor configuration. Under plug-flow conditions, for example, in a tubular, trickle bed, or simulated moving be reactor, the pressure should be sufficient to prevent boiling within the catalyst bed. The preferred operating pressure is in the range of about 0.7 bara up up to about 60 bara (approximately 10–870 psi) and more preferably, 1 bara up to about 40 bara (approximately 14.5–580 psia).

Preferably, the reaction of 2-KLG reactant to L-ascorbic acid is taken to only partial conversion to avoid excessive degradation of the L-ascorbic acid product. The term "conversion" is defined as the total moles of 2-KLG reactant reacted to L-ascorbic acid and by-products divided by the total moles of 2-KLG reactant introduced into the reactor. By partial conversion, it is meant that a portion of the 2-KLG reactant is reacted to L-ascorbic acid, typically in a range of about 10% up to about 90%, or more preferably, in a range of about 20% up to about 80%. A conversion of 2-KLG reactant to L-ascorbic acid in a range of about 40% up to about 70% is especially preferred.

Our process may be operated at any space velocity which provides the desired conversion and selectivity given the temperature, pressure, and catalyst used. The term "space velocity" is defined as the volumetric rate of addition of the solution divided by volume of the reactor. Although, the space velocity may vary over a wide range and is likely to be determined empirically, the preferred range of space velocities is about 0.05 h$^{-1}$ to about 500 h$^{-1}$. More preferably, the range of space velocities is about 0.1 h$^{-1}$ to about 100 h$^{-1}$.

The highly porous nature and high surface areas of the alkaline earth silicate catalysts results in an unusually high absorption capacity. In other uses, it is not unusual for the materials to absorb 2–5 times their weight in water or oils. For example, the alkaline earth silicates have a particular affinity for carboxylic acids and can be used to separate carboxylic acids from cooking oils.

In the practice of this invention, the alkaline earth silicates have a moderate affinity for 2-KLG esters, typically adsorbing up to ca. 30–80% of their own weight of 2-KLG ester, although more or less 2-KLG ester can be absorbed depending upon the composition and source of the catalyst. The alkaline earth silicates generally have a stronger affinity for 2-KLG typically adsorbing 2–3 times their own weight of 2-KLG, although more or less 2-KLG acid can be adsorbed depending upon the composition and source of the catalyst. This affinity of the catalyst for 2-keto-L-gulonic acid or derivatives of 2-KLG can be accounted for in the practice of the present invention. In practice, the adsorbent nature of the catalyst leads to a distinct lag time during the initiation of the reaction in which the 2-KLG compound is adsorbed on the catalyst, with little 2-KLG acid compound observed in the effluent of a continuous reactor. In batch reactors, no 2-KLG acid starting material is observed in the liquid phase until the capacity of the alkaline earth silicate is exceeded.

After passage through the reactor, a solution comprising L-ascorbic acid and unreacted 2-KLG reactant is continuously removed from the reactor and the unreacted 2-KLG reactant is separated and recovered from the L-ascorbic acid product to produce an enriched L-ascorbic acid. By the term "enriched", it is meant that the concentration or assay of L-ascorbic acid is greater than the L-ascorbic acid present in the reactor effluent. Generally, the unreacted 2-KLG reactant is recovered as a solution in the reaction solvent but may also be recovered in solid form. Although the unreacted 2-KLG reactant may be recycled to the reactor as a solid, it is preferred to recycle the 2-KLG reactant to the reactor as a solution.

There a numerous methods of separating the 2-KLG reactant from L-ascorbic acid well known to those skilled in the art. Examples of separation techniques include fractional crystallization, electrodialysis membrane separation, chromatographic methods, and the like. Crystallization is often used to isolate L-ascorbic acid from 2-KLG and esters of 2-KLG Electrodialysis membranes operated with anion exchange resins may be used to separate ascorbic acid from 2-KLG as the two components have differing pKa's as described in European Patent Application No. 0 554 090 A2 and U.S. Pat. No. 4,767,870. Once separated, the 2-KLG may be recycled back to the conversion step and the ascorbic acid may be recovered. In addition, a variety of chromatographic methods are capable of separating 2-KLG or derivatives of 2-KLG from ascorbic acid. For example, U.S. Pat. No. 5,817,238 describes a process for recovery of ascorbic acid from a filtrate solution obtained in the crystallization of ascorbic acid. Alternatively, the ascorbic acid may be adsorbed onto a resin, and then desorbed using a neutral solvent in which the concentration of the ascorbic acid in the eluent is at least as concentrated as the ascorbic acid in the aqueous feed stream as describe in International Patent Application No. 97/13761.

With any of the aforementioned separations, unreacted 2-KLG compounds may be recovered and recycled to the reactor. The recycled 2-KLG ester may be purified and concentrated prior being recycled to the reactor. The presence of a subsequent product separation units, purification units, and recycle loops would be expected and are encompassed within the scope of this invention.

The various embodiments of the present invention are further illustrated by the following examples.

EXAMPLES

Example 1

A solution of 2-keto-L-gulonic acid (designated hereinafter as "2-KLG") was obtained by fermentation of glucose using genetically modified *Pantoea citrea* followed by partial purification via microfiltration and electrodialysis. The aqueous solution obtained by this method contained 22.6 wt. % 2-KLG and 0.30 wt. % L-ascorbic acid as determined by high pressure liquid chromatographic analysis. This solution was used as feedstock throughout this experiment.

The reactor consisted of a cylindrical steam jacketed column measuring 2.5 cm (ID)×15 cm (CHROMOFLEX® AQ Borosilicate Glass Chromatography column, VWR Cat. No. KT425870-2515; VWR, Buffalo Grove, Ill.) filled with 30–60 mesh (250–600 μm) FLORISIL® magnesium silicate (Product of US Silica; 15 wt. % MgO: 85% $SiO_2$) clamped in a vertical position. The base (inlet) of the reactor was connected to the outlet of an HPLC (High Pressure Liquid Chromatography) pump via TEFLON® tubing (0.318 cm ($\frac{1}{8}^{th}$ in) OD, 0.16 cm ($\frac{1}{16}^{th}$ in) ID). All TEFLON® tubing used in this experiment was of the same dimension and used PFTE fittings for connections. The top (outlet) of the column was connected via TEFLON® tubing to a receiver that was inserted under a nitrogen atmosphere. The inlet of the HPLC pump was connected to a reservoir of the 2-KLG feedstock solution via TEFLON® tubing. A 10 μm polyethylene filter was attached to the inlet to protect the pump. The reactor was heated with steam throughout the experiment. A flow rate of 0.5 mL/min was established using the HPLC pump and samples taken over a 9.6 hr period.

The samples were analyzed by high pressure liquid chromatography using an Inertsil ODS2 Keystone Scientific Part # 155-181, 150×4.6, 5 μm (DraChrom; Greensboro, N.C.; Cat # 155-181) column and an Applied Biosystems 783a Programmable Absorbance Detector (detection wavelength: 205 nm). The mobile phase consisted of a solution of 10.55 g mono basic potassium phosphate, 3.4 g tetrabutylammonium phosphate, and 2.59 mL concentrated phosphoric acid diluted to 1000 mL in a volumetric flask with distilled water. The analytical sample was prepared by diluting 125 μL of the liquid sample from the reactor to 50 mL with water. A 5 μL sample was added to the column and eluted using a flow rate of 1.0 mL/min. Quantification was accomplished by comparison with the response for a range of standard solutions prepared by dissolving recrystallized 2-KLG and L-ascorbic acid in water at various concentrations.

Analysis indicated that the reaction did not reach steady state until 5.3 h had elapsed. Over the remaining 4.3 h, the average concentration of 2-KLG in the effluent was 18.2 wt. % 2-KLG and 3.0 wt. % L-ascorbic acid. This represented a 19% conversion of 2-KLG with a 75% selectivity to L-ascorbic. Convention and selectivity are defined and used hereinafter as follows:

Conversion=(molar concentration of KLG reactant in the reactor effluent)/(molar concentration of KLG reactant in the feed)

Selectivity of conversion=(molar concentration of ascorbic acid product)/(molar concentration of KLG reactant in the feed−molar concentration of KLG reactant in the product)

The addition rate of feedstock solution was then reduced to 0.25 mL/min over a period of 9.1 hours. A new steady state was achieved in 5 hours. Over the remaining 4.1 h, the average concentration of 2-KLG in the effluent was 15.2 wt. % 2-KLG and 5.4 wt. % L-ascorbic acid. This represented a 33% conversion of 2-KLG with an 81% selectivity to L-ascorbic acid.

In the last phase, the addition rate of feedstock solution was reduced to 0.13 mL/min over a period of 22.7 hours. A period of 15 hrs was provided to achieve a new steady state and samples removed thereafter over a period of 7.7 hrs. Over the remaining 4.1 h, the average concentration of KLG in the effluent was 11.5 wt. % 2-KLG and 6.4 wt. % L-ascorbic acid. This represented a 49% conversion of 2-KLG with a 63% selectivity to L-ascorbic acid. These results are summarized in Table 1 below.

TABLE 1

Conversion of 2-Keto-L-Gulonic Acid to L-Ascorbic Acid Using FLORISIL ® magnesium silicate (15 wt. % MgO: $SiO_2$)

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 0.50 mL/min | 18.2 wt. % | 3.0 wt. % | 19% | 75% |
| 0.25 mL/min | 15.2 wt. % | 5.4 wt. % | 33% | 81% |
| 0.13 mL/min | 11.5 wt. % | 6.4 wt. % | 49% | 63% |

Example 2

Example 1 was repeated using MAGNESOL® magnesium silicate powder (The Dallas Group of America, Jeffersonville, Ind.; molar ratio 1 MgO: 2.6 $SiO_2$ .$H_2O$) and a feedstock containing 22.9 wt. % 2-KLG and 0.3 wt. % L-ascorbic acid. The results at each feed rate are recorded in Table 2.

TABLE 2

Conversion of 2-Keto-L-Gulonic Acid to L-Ascorbic Acid Using MAGNESOL ® magnesium silicate (1 MgO: 2.6 $SiO_2$.$H_2O$)

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 0.50 mL/min | 18.5 wt. % | 2.4 wt. % | 19% | 60% |
| 0.25 mL/min | 14.9 wt. % | 5.1 wt. % | 35% | 70% |
| 0.13 mL/min | 10.4 wt. % | 6.2 wt. % | 55% | 54% |

Example 3

Example 1 was repeated using calcium silicate powder ($CaSiO_3$, Sigma-Aldrich) and a feedstock containing 22.8 wt. % 2-KLG and 0.3 wt. % L-ascorbic acid. The results at each feed rate are recorded in Table 3

TABLE 3

Conversion of 2-Keto-L-Gulonic Acid to L-Ascorbic Acid Using Calcium Silicate ($CaSiO_3$)

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 0.50 mL/min | 17.3 wt. % | 3.4 wt. % | 24% | 67% |
| 0.25 mL/min | 13.7 wt. % | 5.8 wt. % | 40% | 69% |
| 0.13 mL/min | 9.3 wt. % | 6.6 wt. % | 59% | 53% |

Comparative Example 1

Example 1 was repeated using crushed quartz as an inert, non-catalytic packing and a feedstock containing 23.0 wt. % 2-KLG and 0.3 wt. % L-ascorbic acid. The results at each feed rate are recorded in Table C-1. The results illustrate the extent of the self-catalyzed thermal lactonization of 2-KLG and, in view of Tables 1–3, further show the catalytic effect of the alkaline earth silicates.

TABLE C-1

Comparative Example Showing Conversion of 2-Keto-L-Gulonic Acid to L-Ascorbic Acid Using Quartz as an Inert Packing

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 0.50 mL/min | 20.9 wt. % | 1.6 wt. % | 9% | 80% |
| 0.25 mL/min | 18.9 wt. % | 2.8 wt. % | 18% | 74% |
| 0.13 mL/min | 15.9 wt. % | 3.4 wt. % | 31% | 52% |

Comparative Example 2

Example 1 was repeated using magnesium aluminate ($MgAl_2O_7$; Aldrich) and a feedstock containing 22.2 wt. % 2-KLG and 0.4 wt. % L-ascorbic acid. The results at each feed rate are recorded in Table C-2 and show little or no catalytic effect from alkaline earth aluminates.

TABLE C-2

Comparative Example showing Conversion of 2-Keto-L-Gulonic Acid to L-Ascorbic Acid Using Magnesium Aluminate

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 0.50 mL/min | 20.4 wt. % | 1.7 wt. % | 8% | 100% |
| 0.25 mL/min | 18.9 wt. % | 2.3 wt. % | 15% | 76% |
| 0.13 mL/min | 14.2 wt. % | 2.8 wt. % | 36% | 38% |

Example 4

This example describes results using a plug flow reactor for preparation of L-ascorbic acid from 2-keto-L-gulonic acid. A solution of 2-KLG was obtained by fermentation of glucose using genetically modified *Pantoea citrea* followed by partial purification via microfiltration, electrodialysis, and subsequent crystallization which provides the monohydrate of 2-keto-L-gulonic acid. An aqueous solution of 2-KLG was prepared from this material by dissolving 110 g the monohydrate obtained above in 890 mL of water. The resultant solution contained 10.41 wt. % 2-KLG and 0.05 wt. % L-ascorbic acid by analysis. This solution was used as feedstock throughout this experiment.

The feed system to the reactor consisted of a reservoir of aqueous 2-keto-L-gulonic acid, whose preparation and composition was described above, connected to a high pressure liquid chromatography (HPLC) pump via using 0.318 cm ($\frac{1}{8}^{th}$ in) OD (0.16 cm ($\frac{1}{16}^{th}$ in) ID) high pressure TEFLON® tubing. The outlet of the HPLC pump was connected via 0.318 cm ($\frac{1}{8}^{th}$ in) OD (0.16 cm ($\frac{1}{16}^{th}$ in) ID) high pressure TEFLON® tubing to a pressure relief valve (set at 50 psi) followed by a pressure gauge (both constructed of 316 Stainless Steel) assembled in series using appropriate PFA reducing unions to connect the assembly to the HPLC pump.

The reactor consisted of a 74 cm (29 in) length of PFA tubing wall thickness of 0.16 cm ($\frac{1}{16}^{th}$ in) and an outside diameter of 0.95 cm ($\frac{3}{8}^{th}$ in) (Reactor volume=21 mL). The ends of the tube were fitted with PFA pressure fittings. The reactor was then filled by:

1) placing a small glass wool plug in the end of the reactor;
2) adding a small quantity of coarse sand (ca. 1 cm);
3) adding 30–60 mesh (250–600 $\mu$m) FLORISIL® magnesium silicate (15% MgO: 85% $SiO_2$) to within ca. 1.5 cm of the top with continuous light tapping to insure good packing;
4) adding another small amount of coarse sand (ca. 1 cm.); and
5) adding another glass wool plug.

The outlet of feed system was attached to the inlet of the reactor using 0.318 cm ($\frac{1}{8}^{th}$ in) OD (0.16 cm ($\frac{1}{16}^{th}$ in) ID) high pressure TEFLON® tubing and appropriate PFA reducing unions. For safety, care should be taken to maintain the temperature and pressure of the reactor system within the operating limits recommended by the manufacturer of the tubing, valves, fittings, and other components. The reactor was immersed in a circulating oil bath.

The outlet of the reactor was attached to a 75 cm length of 0.318 cm ($\frac{1}{8}^{th}$ in) OD (0.16 cm ($\frac{1}{16}^{th}$ in) ID) high pressure TEFLON® tubing using appropriate PFA reducing unions. The length of 0.318 cm ($\frac{1}{8}^{th}$ in) OD (0.16 cm ($\frac{1}{16}^{th}$ in) ID) high pressure TEFLON® tubing was placed in a room temperature water bath and the outlet connected to a pressure gauge (316 Stainless Steel) using 0.16 cm ($\frac{1}{16}^{th}$ in) high pressure PFA tubing and appropriate PFA reducing unions. The pressure gauge was then attached to a back-pressure regulator (316 Stainless Steel), which was used to maintain the pressure in the reactor above the vapor pressure of the solvent (water). The outlet of the backpressure regulator was attached to a length of 0.318 cm ($\frac{1}{8}^{th}$ in) OD (0.16 cm ($\frac{1}{16}^{th}$ in) ID) high pressure TEFLON® tubing using appropriate PFA reducing unions which led into a receiving vessel (round bottom flask). A nitrogen atmosphere was maintained by placing a gas inlet with a septum on top of a round bottom flask and piercing the septum with the 0.318 cm ($\frac{1}{8}^{th}$ in) OD (0.16 cm ($\frac{1}{16}^{th}$ in.) ID) high pressure TEFLON® tubing and attaching the gas inlet to a nitrogen source. The size of the round bottom flask was varied based on the flow rate and length of time between samples. Generally, a 50 mL or a 100 mL flask was adequate.

The temperature of the oil bath (containing the reactor) was raised to 140° C. and the HPLC pump was started at an initial flow rate of 1.40 mL/min. The reaction was allowed to flow through the reactor until it reached steady state which is achieved in about 90 minutes (ca. 125 mL of 10.4 wt. % 2-KLG solution). At steady state, seven samples were removed and analyzed by HPLC using the same analytical procedure as in Example 1. The flow rate was reduced in stages to a final flow rate of 0.60 mL/min. At each stage, passage of ca. 125 mL of 10.4 wt. % 2-KLG solution was required to achieve the new state. At each flow rate, nine samples were removed at steady state and each was analyzed by HPLC. The average composition at each flow rate is recorded in Table 4 along with the conversion and selectivity at each flow rate.

TABLE 4

Conversion of 2-Keto-L-Gulonic Acid to L-Ascorbic Acid Using FLORISIL ® magnesium silicate at 140° C.

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 1.40 mL/min | 7.33 wt. % | 1.7 wt. % | 28% | 88% |
| 1.20 mL/min | 7.07 wt. % | 2.3 wt. % | 31% | 92% |
| 1.00 mL/min | 6.46 wt. % | 2.8 wt. % | 37% | 87% |
| 0.90 mL/min | 5.99 wt. % | 3.27 wt. % | 43% | 81% |
| 0.80 mL/min | 5.43 wt. % | 3.41 wt. % | 46% | 82% |
| 0.70 mL/min | 5.02 wt. % | 3.81 wt. % | 52% | 85% |
| 0.60 mL/min | 4.47 wt. % | 4.16 wt. % | 57% | 84% |

Comparative Example 3

The procedure in Example 4 was repeated using 30–60 mesh (250–600 $\mu$m) ground quartz (as an inert filler) instead of the 30–60 mesh (250–600 $\mu$m) FLORISIL® magnesium silicate (15% MgO: 85% $SiO_2$). The reaction was operated alongside Example 4 using the same feed solution, immersed in the same circulating oil bath, and at the same time. The results appear in Table C-3. When compared to Example 6, it was found that the reaction was accelerated by the presence of FLORISIL® magnesium silicate.

TABLE C-3

Conversion of 2-Keto-L-Gulonic Acid to L-Ascorbic Acid Using Quartz (as an Inert Packing) at 140° C.

| Flow Rate of 2-Keto-L-Gulonic Acid Feed Solution | Average Exit Concentration of 2-Keto-L-Gulonic Acid | Average Exit Concentration of L-Ascorbic Acid | 2-Keto-L-Gulonic Acid Conversion | Selectivity to L-Ascorbic Acid |
|---|---|---|---|---|
| 1.40 mL/min | 8.48 wt. % | 1.42 wt. % | 18% | 86% |
| 1.20 mL/min | 8.24 wt. % | 1.69 wt. % | 21% | 88% |
| 1.00 mL/min | 7.98 wt. % | 1.95 wt. % | 22% | 95% |
| 0.90 mL/min | 7.19 wt. % | 2.47 wt. % | 29% | 92% |
| 0.80 mL/min | 6.85 wt. % | 2.61 wt. % | 33% | 87% |
| 0.70 mL/min | 6.97 wt. % | 2.55 wt. % | 33% | 80% |
| 0.60 mL/min | 6.51 wt. % | 2.86 wt. % | 38% | 79% |

Example 5

The following example describes the generation of L-ascorbic acid from 2-KLG ester in a plug-flow reactor using the methods of the present invention. A solution of 2-KLG was obtained by fermentation of glucose using genetically modified *Pantoea citrea* followed by partial purification via microfiltration, electrodialysis, and subsequent crystallization which provides the monohydrate of 2-keto-L-gulonic acid.

To convert the crystalline 2-KLG monohydrate to the methyl ester (MKLG), 140 g (660 mmol) KLG was dissolved in 1000 mL of methanol in a 2L flask with stirring. The flask was cooled in an ice/water bath and hydrochloric acid (HCl) was bubbled through until the mixture was saturated (less than 10 minutes). The solution was left to stir for 1 hour at which time there was no starting material left as determined by thin layer chromatography (1:4 MeOH/CHCl$_3$, stained in phosphomolybdic acid/ethanol solution). The solution was filtered, washed with cold methanol and dried overnight in a desiccator to afford 45.98 g of MKLG (yield 33%). Two more crops were obtained to afford an additional 67.05 g (82.5% overall yield) by reducing solution volume (i.e. distillation under reduced pressure followed by cooling). Analysis by HPLC showed the product to be 98.5% MKLG, 1.4% KLG and 0.1% L-ascorbic acid (AsA).

A methanolic solution of 2-KLG methyl ester was prepared by dissolving 60 g of the 2-KLG methyl ester (MKLG) generated above in 540 g of methanol. The resultant solution contained 10.66 wt. % 2-KLG methyl ester and 0.01 wt. % L-ascorbic acid by HPLC analysis and had a density of 0.868 g/mL. This solution was used as feedstock throughout the experiment.

The feed system to the reactor consisted of a reservoir of the methanolic 2-KLG methyl ester (described above) connected to a high pressure liquid chromatography (HPLC) pump using high pressure TEFLON® tubing (0.318 cm ($1/8^{th}$ in) outer diameter (OD) and 0.16 cm ($1/16^{th}$ in.) inner diameter (ID)). All TEFLON® tubing used in this experiment was of the same dimensions and where applicable, used PFTE fittings for connections. The outlet of the HPLC pump was connected via high pressure TEFLON® tubing to a pressure relief valve set at 50 pounds per square inch (psi) followed by a pressure gauge (both constructed of 316 Stainless Steel) assembled in series using appropriate PFA reducing unions to connect the assembly to the HPLC pump. The reactor was the same reactor used in Example 6 above except that since the solvent was methanol, the backpressure regulator was used to maintain the pressure in the reactor above the vapor pressure of methanol (rather than water as for KLG).

For the synthesis of L-ascorbic acid from the methyl ester of 2-keto-L-gulonic acid, the temperature of the oil bath (containing the reactor) was raised to 110° C. and the HPLC pump was started at a flow rate of 0.80 mL/min. The reaction was allowed to flow through the reactor until it reached steady state which was achieved after about 75 minutes. At steady state, five samples were removed over a period of about 4.5 hrs.

The samples were analyzed by High Pressure Liquid Chromatography using an Inertsil ODS2 Keystone Scientific Part # 155-181, 150×4.6, 5 um (DraChrom Cat # 155-181, DraChrom, Greensboro, N.C.) column and an Applied Biosystems 783a Programmable Absorbance Detector (detection wavelength: 205 nm). The mobile phase consisted of a solution of 10.55 grams (g) mono basic potassium phosphate, 3.4 g tetrabutylammonium phosphate, and 2.59 mL concentrated phosphoric acid diluted to 1000 mL in a volumetric flask with distilled water. The analytical sample was prepared by diluting 125 μL of the liquid sample from the reactor to 50 mL with water. A 5 μL sample was added to the column and eluted using a flow rate of 1.0 mL/min. Quantification was accomplished by comparison with the response for a range of standard solutions prepared by dissolving recrystallized 2-KLG methyl ester and L-ascorbic acid in water at various concentrations.

The average concentration of the effluent from the reactor was 7.99% 2-KLG methyl ester and 1.86% L-ascorbic acid. This represents a 25% conversion of 2-KLG methyl ester with a selectivity to L-ascorbic acid of 81%. Selectivity is defined as described below:

Selectivity of conversion=(molar concentration of ascorbic acid product)/(molar concentration of MKLG in the feed)−(molar concentration of MKLG in the product).

The reactor was allowed to cool overnight and was returned to steady state at the same temperature the following day. The reactor was operated at steady state for 5.5 hours taking six samples. The samples were analyzed in the same manner and demonstrated an effluent concentration of 9.41% 2-KLG methyl ester and 1.00% L-ascorbic acid. This represents a 12% conversion of 2-KLG methyl ester with a selectivity to L-ascorbic acid of 94%. Thus, even with a prolonged period on line, the catalyst of the present invention remains substantially active and generates ascorbic acid with a high selectivity. Similar levels of conversion were found for reactors after three days on line.

There is no discernible conversion of the 2-KLG to L-ascorbic acid in a tube packed with quartz indicating that, unlike the corresponding carboxylic acid form of 2-keto-L-gulonic acid, the methyl ester of 2-KLG does not undergo any significant thermal conversion to L-ascorbic acid.

We claim:

1. A process for preparing an ascorbic acid comprising contacting a 2-keto-hexonic acid; a 2-keto-hexonic acid derivative selected from esters, acetals, hemiacetals, ketals, hemiketals, and ethers of a 2-keto-hexonic acid; or a mixture thereof with a catalyst comprising at least one alkaline earth silicate with the proviso that the alkaline earth silicate is not a zeolite.

2. A process according to claim 1 wherein the 2-keto-hexonic acid is 2-keto-L-gulonic acid (2-KLG) or 2-keto-D-gluconlc acid (2-KDG).

3. A process according to claim 2 wherein the ascorbic acid is L-ascorbic acid or D-araboascorbic acid.

4. A process according to claim 3 wherein the 2-KLG or 2-KDG ester is prepared from an alcohol containing from 1 up to about 12 carbon atoms.

5. A process according to claim 4 wherein the 2-keto-hexonic acid, the 2-keto-hexonic acid derivative, or the mixture thereof further comprises a solvent selected from the group consisting of water, alcohols, esters, ethers, amides, sulfoxides, sulfones, nitriles, ketones, aldehydes, and mixtures thereof.

6. A process according to claim 5 wherein the alkaline earth silicate catalyst is a composition or a mixture of compositions comprising at least a one compound of an alkaline earth metal selected from the group consisting of berylium, magnesium, calcium, strontium, and barium; and silica wherein the gram-atom ratio of alkaline earth metal to silicon is in the range of about 1:20 to about 20:1 gram-atom alkaline earth metal:gram-atom silicon.

7. A process for the preparation of L-ascorbic acid comprising contacting a water, methanol, or ethanol solution comprising a 2-KLG reactant with a catalyst comprising at least one alkaline earth silicate, with the proviso that the alkaline earth silicate is not a zeolite, at reaction condition of temperature and pressure wherein the gram-atom ratio of alkaline earth metal to silicon is in the range of about 1:5 to about 5:1 gram-atom alkaline earth metal:gram-atom silicon and wherein the catalyst has a surface area in the range of about 50 m$^2$/gram up to about 300 m$^2$/gram.

8. A process according to claim 7 wherein the 2-KLG reactant is selected from the group consisting of 2-KLG, the methyl ester of 2-KLG, the ethyl ester of KLG, and mixtures thereof.

9. A process according to claim 8 wherein the alkaline earth silicate catalyst is a composition or mixture of compositions comprising at least a one compound of an alkaline earth metal selected from the group consisting of magnesium, calcium, and mixtures thereof; and silica.

10. A process for the continuous preparation of L-ascorbic acid comprising the steps of (i) continuously feeding a water, methanol, or ethanol solution comprising a 2-KLG reactant selected from the group consisting of 2-KLG, the methyl ester of 2-KLG, the ethyl ester of 2-KLG, and mixtures thereof to a reactor operated under substantially plug-flow conditions and maintained at reaction conditions of temperature and pressure; (ii) contacting the feed solution from step(i) with a catalyst selected from the group consisting of a calcium silicate, a calcium-magnesium silicate, a magnesium silicate, and mixtures thereof wherein a portion of the 2-KLG reactant is reacted to form L-ascorbic acid; (iii) continuously removing a solution comprising L-ascorbic acid and unreacted 2-KLG reactant from the reactor; (iv) separating and recovering the unreacted 2-KLG reactant from the L-ascorbic acid to produce an enriched L-ascorbic acid and a solution comprising the 2-KLG reactant; and (v) recycling the recovered 2-KLG reactant solution of step(iv) to step(i).

11. A process according to claim 10 wherein the 2-KLG reactant is the product of a fermentation process.

12. A process according to claim wherein the catalyst is selected from the group consisting of entastite ($MgSiO_3$), talc ($Mg_3Si_4O_{10}$), serpentine ($Mg_2Sl_2O_5(OH)_2$), wollastonite ($CaSiO_3$), diopside ($CaMgSi_2O_6$), akermanite ($Ca_2MgSl_2O_7$), and montcellite ($CaMgSiO_4$).

13. A process according to claim 12 wherein the catalyst is a magnesium silicate comprising 15 wt. % MgO: 85 wt. % $SiO_2$, a magnesium silicate comprising the general formula 1 MgO: 2.6 $SiO_2.H_2O$, or a calcium silicate.

14. A process according to claim 9 or 13 wherein the temperature is in the range of about 100° C. up to about 175° C. and the pressure is in the range of about 1 bar absolute up to about 40 bars absolute.

15. A process according to claim 14 wherein the reactor is a trickle bed reactor or simulated moving bed reactor.

\* \* \* \* \*

UNITED STATES PATENT AND TRADEMARK OFFICE
CERTIFICATE OF CORRECTION

PATENT NO. : 6,740,762 B2
DATED : May 25, 2004
INVENTOR(S) : Zoeller et al.

It is certified that error appears in the above-identified patent and that said Letters Patent is hereby corrected as shown below:

Column 18,
Line 64, reads "alkaline earth silicate is not a zeolite, at reaction condition" but should read -- alkaline earth silicate is not a zeolite, at reaction conditions --

Column 20,
Line 8, reads "12. A process according to claim wherein the catalyst is" but should read -- 12. A process according to claim 11 wherein the catalyst is --
Line 10, reads "talc ($Mg_3Si_4O_{10}$), serpentine ($Mg_2Sl_2O_5(OH)_2$), wollasto-" but should read -- talc ($Mg_3Si_4O_{10}$), serpentine ($Mg_2Si_2O_5(OH)_2$), wollasto- --
Line 12, reads "($Ca_2MgSl_2O_7$), and montcellite ($CaMgSiO_4$)" but should read -- ($Ca_2MgSi_2O_7$), and montcellite ($CaMgSiO_4$) --

Signed and Sealed this

Twenty-fifth Day of January, 2005

JON W. DUDAS
*Director of the United States Patent and Trademark Office*